United States Patent
Loveday

(10) Patent No.: US 9,797,869 B2
(45) Date of Patent: Oct. 24, 2017

(54) SYSTEM FOR MONITORING THE CONDITION OF STRUCTURAL ELEMENTS AND A METHOD OF DEVELOPING SUCH A SYSTEM

(75) Inventor: Philip Wayne Loveday, Midrand (ZA)

(73) Assignee: CSIR, Pretoria (ZA)

( * ) Notice: Subject to any disclaimer, the term of this patent is extended or adjusted under 35 U.S.C. 154(b) by 340 days.

(21) Appl. No.: 14/239,666

(22) PCT Filed: Aug. 23, 2012

(86) PCT No.: PCT/IB2012/054264
§ 371 (c)(1),
(2), (4) Date: Apr. 14, 2014

(87) PCT Pub. No.: WO2013/027187
PCT Pub. Date: Feb. 28, 2013

(65) Prior Publication Data
US 2014/0238139 A1    Aug. 28, 2014

(30) Foreign Application Priority Data
Aug. 23, 2011   (ZA) ................. 2011/06192

(51) Int. Cl.
  *G01N 29/04*   (2006.01)
  *G01N 29/34*   (2006.01)
  (Continued)

(52) U.S. Cl.
  CPC ............ *G01N 29/34* (2013.01); *G01N 29/04* (2013.01); *G01N 29/043* (2013.01);
  (Continued)

(58) Field of Classification Search
  CPC ...... G01N 29/04; G01N 29/44; G01N 29/043; G01N 29/221; G01N 29/262
  (Continued)

(56) References Cited

U.S. PATENT DOCUMENTS 5,462,244 A * 10/1995 Van Der Hoek ......... B61L 1/06
                                                      246/122 R
7,938,008 B2 * 5/2011 Owens ................. G01N 29/043
                                                      73/599

(Continued)

FOREIGN PATENT DOCUMENTS

WO   2004098974 A1   11/2004
ZA      996936 A     1/2000

OTHER PUBLICATIONS

International Search Report for PCT/IB2012/054264, international filing date of Aug. 23, 2012, mailed Jun. 18, 2013, 6 pages.
(Continued)

*Primary Examiner* — Helen Kwok
(74) *Attorney, Agent, or Firm* — Cantor Colburn LLP

(57) ABSTRACT

A system for monitoring the condition of elongate structural elements, for example, railway rails, and a method of designing and manufacturing the system is disclosed. The method includes identifying and selecting suitable modes of propagation and signal frequencies that can be expected to travel large distances through an elongate structural element; designing a transducer that will excite the selected mode at the selected frequency; numerically modelling the transducer as attached to the elongate structural element; validating the transducer design by analyzing a harmonic response of the selected mode of propagation to excitation by the transducer, and manufacturing one or more transducers for use in the system.

8 Claims, 3 Drawing Sheets

(51) Int. Cl.
 G01N 29/44 (2006.01)
 G06F 17/50 (2006.01)
(52) U.S. Cl.
 CPC ..... *G01N 29/4472* (2013.01); *G06F 17/5009* (2013.01); *G01N 2291/042* (2013.01); *G01N 2291/048* (2013.01); *G01N 2291/102* (2013.01); *G01N 2291/106* (2013.01); *G01N 2291/2623* (2013.01)
(58) Field of Classification Search
 USPC .................................................. 73/632, 602
 See application file for complete search history.

(56) References Cited

U.S. PATENT DOCUMENTS

| | | | | |
|---|---|---|---|---|
| 8,365,600 | B2* | 2/2013 | Kroning | 73/602 |
| 2004/0093949 | A1* | 5/2004 | Alleyne | B61K 9/10 73/625 |
| 2010/0050087 | A1* | 2/2010 | Sherrard | G06F 3/04817 715/739 |

OTHER PUBLICATIONS

Loveday, Philp W., "Development of piezoelectric transducers for a railway integrity monitoring system," In Smart Structures and Materials 2000: Smart Systems for Bridges, Structures, and Highways, S.C. Liu Editor, Proceedings of SPIE, Apr. 20, 2000, vol. 3988, pp. 330-338; Downloaded From http://proceedings.spiedigitallibrary.org/on Dec. 12, 2012 Terms of Use: http://spiedl.org/terms, pp. 330-338.

Loveday, Philip W., "Simulation of Piezoelectric Excitation of Guided Waves Using Waveguide Finite Elements," IEEE Transactions on Ultrasonics, Ferroelectrics, and Frequency Control, IEEE, US, vol. 55, No. 9, Sep. 1, 2008, pp. 2038-2045.

Loveday, Philip W., "Analysis of Piezoelectric Ultrasonic Transducers Attached to Waveguides Using Waveguide Finite Elements," IEEE Transactions on Ultrasonics, Ferroelectrics, and Frequency Control, IEEE, US, vol. 54, No. 10, Oct. 1, 2007, pp. 2045-2051.

Rose, Joseph L., et al., "Guided wave inspection potential of defects in rail," NDT&E International, Butterworth-Heinemann, Oxford, GB, vol. 37, No. 2, Mar. 1, 2004, pp. 153-161.

Ryue, J., et al., "Decay rates of propagating waves in railway tracks at high frequencies," Journal of Sound and Vibration, London, GB, vol. 320, No. 4-5, Mar. 6, 2009, pp. 955-976.

English translation and Chinese Office Action dated Apr. 5, 2016 in Corresponding Chinese Application No. 201280041069.8, 9 pages.

Ren, Yuan, "Research on Method for Detecting Real-time Broken Rails based on Ultrasonic Guided Waves," Chinese Master's Theses Full-text Database, the Engineering Science and Technology II, No. 3, 2010, C033-9, Mar. 15, 2011; 38 pages.

Wang, Shu-juan, et al., "3-D Finite Element Analysis and Optimum Design of Eiectromagnetic Acoustic Transducers," Proceedings of the CSEE, vol. 29, No. 30, 2009, pp. 123-128, Oct. 31, 2009.

\* cited by examiner

SYSTEM FOR MONITORING THE CONDITION OF STRUCTURAL ELEMENTS AND A METHOD OF DEVELOPING SUCH A SYSTEM

This application is a U.S. national stage application of International Application No. PCT/IB2012/054264, which has an international filing date of Aug. 23, 2012, and which claims priority to South African Patent Application No. 2011/06192, filed Aug. 23, 2011.

BACKGROUND OF THE INVENTION

THIS invention relates to a system for monitoring the condition of elongate structural elements and more particularly but not exclusively, to a system for monitoring and detecting cracks and breaks in railway rails. The invention furthermore extends to the methodology of designing and developing such a system.

There are several methods and systems which have been proposed for monitoring the integrity of elongate structural elements, and in particular railway rails. These methods and systems are aimed at detecting cracks in the rails before they develop into complete breaks, and also to detect breaks in a railway network where they have already occurred. If a crack or break in the rail is not detected beforehand, it could result in the derailment of the railway vehicle travelling on the track. It will be appreciated that such derailments cause financial loss and can also result in injury and loss of life. Also, it should be noted that although reference is made to railways, these systems are equally applicable to other applications where lengths of structural steel are utilised, such as for example mine shafts and bridges.

One method of detecting cracks and breaks in the rails of railway tracks is disclosed in South African patent 99/6936, the contents of which is incorporated herein by reference. The method includes the step of providing a number of autonomous acoustic transmitter units, and a number of acoustic receiver units located between the transmitter units. The various units are spaced apart from one another by predetermined distances. The transmitter units introduce a series of acoustic pulses with specific frequency composition into the rails and the receiver units detect and analyse the pulses to monitor any unwanted condition concerning the rail. This method requires the use of transmitters and the use of receivers in order to monitor the condition of the rail.

Development of transducers for this method of detecting and monitoring cracks and breaks in railway rails is discussed in "*Development of piezoelectric transducers for a railway integrity monitoring system*", Philip W, Loveday, Smart Structures and Materials 2000: Smart Systems for Bridges, Structures, and Highways, Proceedings of SPIE Vol. 3988, 2000, Newport Beach, pp. 330-338. The system makes use of piezoelectric transducers which are mounted (clamped) under the crown of the rail on the outside of the track. The method of clamping the piezoelectric transducers is described in PCT patent application WO 2004/098974, the content of which is incorporated herein by reference.

The piezoelectric transducers are spaced along the length of the railway network and they periodically transmit ultrasonic waves through the rails. The waves propagate through the track from one transducer towards a downstream transducer which acts as a receiving station. Typically, the transducers are spaced about 1 km apart. If the ultrasonic signal is not detected at the receiver station, the receiver station activates an alarm indicating that the rail either has a crack or is broken.

A disadvantage associated with the above system is that the piezoelectric transducers are attached (clamped) under the crown of the rail on the outside of the track. The piezoelectric transducers are large and cannot be attached under the crown on the inside of the track because they would interfere with the train wheels. The piezoelectric transducers have to be removed from the rail during routine track maintenance because a 'tamping' machine used to re-pack the ballast under the sleepers has wheels that engage the outside of the crown. The removal and re-attachment (which requires re-tightening of the clamps two weeks after re-attachment) of the piezoelectric transducers increases the maintenance cost of the system and results in periods of time when the system is inoperable.

In addition, the existing system is not suited for distance in excess of 1 km, as the transmitted signal is not strong enough, and because the transducer is also not accurately matched to the particular structural element to which it will be attached from a propagation and operating frequency point of view.

The detection systems described above have generally been developed using design methodologies that do not optimally incorporate the use of mathematical modelling techniques in which the transducer and rail response is mathematically modelled, and in which the transducer is then designed in an iterative manner. This resulted in the selection of transducers that are not necessarily optimized for a particular application, and which may result in the transducers being larger than required in practice, whilst also not performing optimally insofar as transmission and receiving of signals are concerned.

It is therefore an object of the invention to provide a system for monitoring and detecting cracks and breaks in railway rails that will address the disadvantages described above.

It is also an object of the invention to provide a piezoelectric transducer for use in the system according to the present invention.

It is a further object of the invention to provide a method for developing a transducer-based failure detection system, which will at least partially overcome the above disadvantages, and which will also be a novel and useful alternative to existing design methodologies.

SUMMARY OF THE INVENTION

According to a first aspect of the invention there is provided a method of developing a transducer-based failure detection system, the method including the steps of:
  identifying modes of propagation and signal frequencies that can be expected to travel large distances through an elongate structural element;
  selecting a suitable mode of propagation and frequency of operation;
  designing a transducer that is adapted to excite the selected mode at the selected frequency;
  numerically modelling the transducer as attached to the elongate structural element; and
  analyzing a harmonic response of the selected mode of propagation to excitation by the transducer in order to validate the transducer design.

The step of identifying modes of propagation and frequencies that can be expected to travel large distances through an elongate structural element preferably comprises the use of a numerical model of a particular rail profile having predetermined material properties.

The selection of a suitable mode of propagation and frequency of operation preferably entails selecting a mode of propagation having low attenuation over a large range of frequencies, and which is relatively insensitive to small changes in rail profile.

The method may include the further steps of iteratively changing dimensions of transducer components in order to achieve an optimal response of the selected mode of propagation at the frequency of operation, and computing a predicted displacement time response of the rail to an electrical excitation of the transducer.

The method may further include a verification phase including the steps of:
  manufacturing a prototype in accordance with the modelled transducer;
  measuring free electrical transmittance of the transducer, and comparing the measured free electrical transmittance with transmittance predicted by the model described above.

The verification phase may also include the steps of:
  attaching the transducer to a predetermined length of the structural element;
  measuring a displacement response on a surface of the structural element; and
  comparing the measured response to the predicted displacement time response.

The verification phase may still further include the steps of performing in-use field measurements in order to confirm excitation of the selected mode, as well as propagation with low attenuation.

According to a second aspect of the invention there is provided a system for monitoring and detecting cracks or breaks in rails of a railway track, the system including a plurality of transducers defining transmitting and receiving stations of the system, characterised in that the transducers are preferably located on the inner sides of the rails.

There is provided for the plurality of transducers to be in the form of a series of single transducers located at predetermined spaced apart positions, with ultrasonic waves periodically being transmitted along the rail from one transducer used as a transmitter to a next transducer used as a receiver.

There is also provided for the plurality of transducers to be in the form of a series of single transducers spaced apart at predetermined intervals, with ultrasonic waves periodically being transmitted along the rail from one transducer used as a transmitter, and reflected by a crack in the rail to the same transducer, which is also used as a receiver.

There is further provided for a plurality of transducers to be located at each predetermined position so as to define an array of transducers. A number of arrays may be provided, with the arrays of transducers spaced apart at predetermined intervals.

In one embodiment the transducers are permanently attached to the rails on the inner sides of the rails.

Preferably, the rails include a web and a crown, and there is provided for the transducers to be attached underneath the crown, or alternatively to the web of the rails.

Advantageously, the transducers are of a geometrical size, shape and configuration enabling the attachment thereof to the rails without interfering with a wheel of a railway vehicle travelling on the rails.

In one embodiment the system is configured such that an upstream transducer transmits an ultrasonic wave along the rail which is received by a downstream transducer if there are no cracks or breaks in the rail. The system is furthermore configured such that if the downstream transducer does not receive the ultrasonic wave transmitted by the upstream transducer, an alarm is triggered, warning of the possible presence of a crack or break in the rail.

In another embodiment the system is configured such that a transducer transmits and ultrasonic wave along the rail, and the same transducer receives the ultrasonic wave if it is reflected by a crack in the rail. The system is furthermore configured such that if the transducer receives the reflected ultrasonic wave, an alarm is triggered, warning of the possible presence of a crack in the rail.

In a still further embodiment the system comprises both the functionalities described above.

In one embodiment, the transducers are spaced apart by distances of about 1 to 3 kilometers. Preferably, the transducers are spaced apart by distances of about 2 kilometers.

Preferably, the transducer is a piezoelectric transducer.

According to another aspect of the invention there is provided a transducer suitable for use in a system for monitoring and detecting cracks or breaks in rails of a railway track, the system including a plurality of transducers defining transmitting and receiving stations of the system, characterised in that the transducers are located on the inner sides of the rails.

BRIEF DESCRIPTION OF THE DRAWINGS

A preferred embodiment of the invention is described by way of a non-limiting example, and with reference to the accompanying drawing in which.

EXAMPLE OF DESIGN METHODOLOGY

Figure 2:
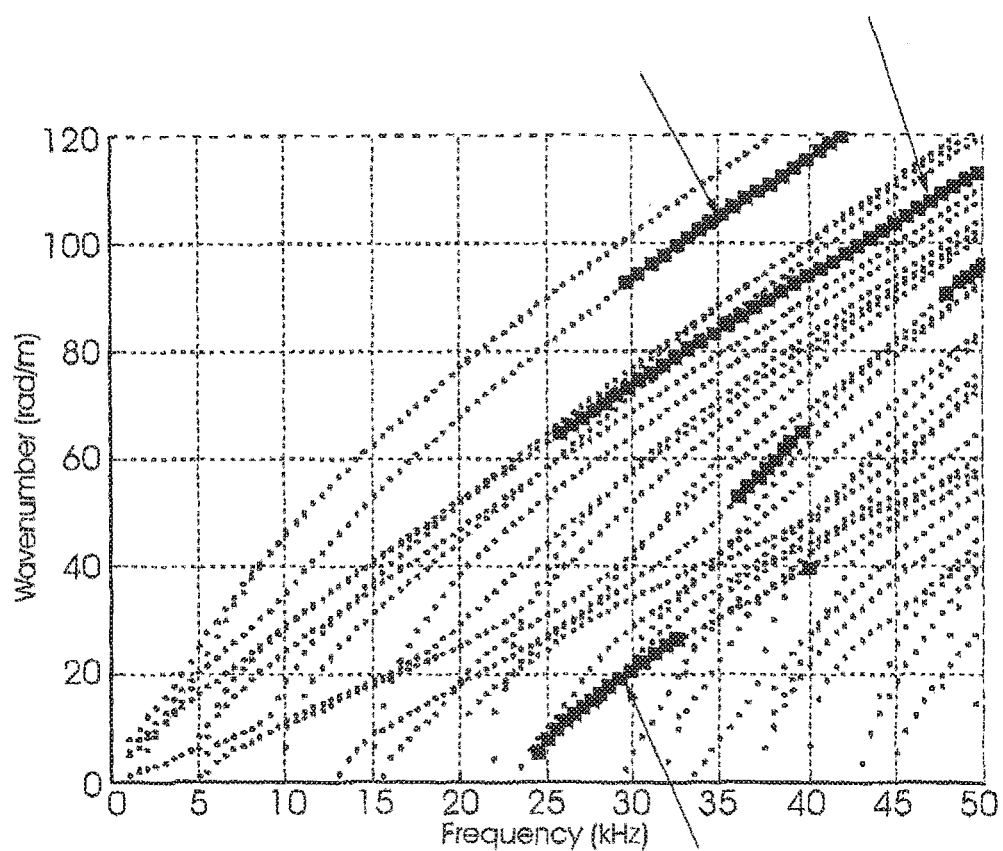
FIG. 2 shows the output of an initial modelling process used to select an appropriate mode of propagation and operating frequency for a particular rail profile.

The methodology and development procedure used to develop a transducer-based failure detection system in accordance with the invention is described with reference to FIG. 2. The method is a computer implemented method.

1. Analysis of Dispersion of Rail Profile on Damped Support.

This step involved developing a numerical (semi-analytical finite element method) model of the rail profile that also incorporated the material properties of the rail. The development of semi-analytical finite element models is a methodology known in the art, but which has not heretofore been applied in this particular application. The model was analysed to determine which modes of propagation and frequencies could be expected to travel large distances. Some modes of propagation and frequencies that were expected to travel with low attenuation are indicated by the arrows in FIG. 2. The size of the dots represents the expected propagation performance. The dots form curves describing different modes of propagation. The arrows indicate three modes that could be suitable and it was accordingly decided to use a signal with a frequency centred at the arrow location.

2. Selection of Appropriate Mode of Propagation and Frequency.

Based on the results from step 1 a mode of propagation and frequency of operation were selected. The selected mode had low attenuation over a reasonably large range of frequencies so that it could be expected to work over a range of temperatures. This analysis is a qualitative procedure in which modes and frequencies with the lowest relative attenuation were considered. The analysis did not attempt to quantify the actual attenuation. Any person skilled in the art will be able to understand and correctly apply this qualitative approach. In essence, if the system is required to detect a particular type of crack the selected mode of propagation should contain energy in the region where the cracks occur. The mode of propagation and range of frequencies was chosen to be relatively insensitive to changes in the rail geometry due to for example rail profile grinding or changes in the axial load in the rail. In this particular example, a mode with wavenumber of 82 rad/m at 35 kHz was selected, and additional analyses were performed to ensure that the selected point was insensitive to rail grinding, temperature changes and axial load.

3. Conceptual Design of Transducer Configuration

A transducer configuration suitable for permanent attachment to a rail was subsequently conceptualized. In this example, a sandwich-type transducer suitable for being attached under a crown of the rail was designed. The transducer design was not fundamentally different in structure and configuration to existing transducer designs, but was expected to be better matched with the system as a whole due to the integrated design methodology.

4. Numerical Modelling of Transducer Configuration Attached to Rail and Sizing to Achieve Large Response at Required Frequency.

A numerical model (3-D finite element method) of the piezoelectric transducer was prepared, and was coupled to the numerical model (semi-analytical finite element method) of the rail. The harmonic response of the selected mode to electrical excitation of the transducer was subsequently analyzed. The dimensions of the transducer components were then iteratively changed in order to achieve an optimal response of the selected mode at the operating frequency. This methodology was previously developed by the inventor, and is described in more detail in "*Simulation of Piezoelectric Excitation of Guided Waves Using Waveguide Finite Elements*", Loveday P W, IEEE Transactions on Ultrasonics, Ferroelectrics, and Frequency control; vol. 54 no. 10; October 2007, the contents of which is incorporated herein by reference. Finally, the predicted displacement time response of the rail due to tone-burst electrical excitation of the transducer was determined for use in a later verification phase. This methodology was also previously developed by the inventor, and is described in more detail in "*Analysis of Piezoelectric Ultrasonic Transducers Attached to Waveguides Using Waveguide Finite Elements*", Loveday P W, IEEE Transactions on Ultrasonics, Ferroelectrics, and Frequency control; vol. 55 no. 9; September 2008, the contents of which is incorporated herein by reference.

5. Transducer Prototype Manufacture and Measurement in Lab.

Based on the above modelling, a number of prototype transducers were manufactured. The free electrical admittance of each transducer was measured and compared with modelled predictions to verify correct manufacture. A transducer was subsequently attached to a short rail length in a lab environment and electrical tone-burst excitation was applied thereto. The displacement response on the rail surface at a distance of 1 m or more was measured using a laser vibrometer. The measured results were then compared to the predicted displacement time response from step 4.

6. Field Measurements to Confirm Transducer Performance and Propagation Mode in Rail.

The transducer was subsequently attached to an actual rail in the field, and was driven electrically. Scanning laser vibrometer measurements were performed on the rail surface at different distances from the transducer (e.g. 5 m, 300 m, 500 m). Modes present in the measured data were extracted to confirm that the selected mode was being excited and that it does indeed propagate with low attenuation. Long-range transmit-receive measurements were performed with the new transducers and compared to the same measurements performed with the prior art transducers.

7. Industrialization of Transducer.

Subsequent to the transducer design process described above, the transducer was industrialised, which process included the preparation of manufacturing data packs and qualification and acceptance test procedures.

The above process yielded an optimised transducer design, which meets the required design criteria, whilst also being of a relatively small size compared to existing transducers used in similar failure detection applications.

The design methodology can furthermore be used in the optimised design of transducers that are application and profile specific, and will therefore result in more accurate design of transducers for use in failure-detection systems.

DESCRIPTION OF AN EMBODIMENT OF THE SYSTEM

Figure 1:
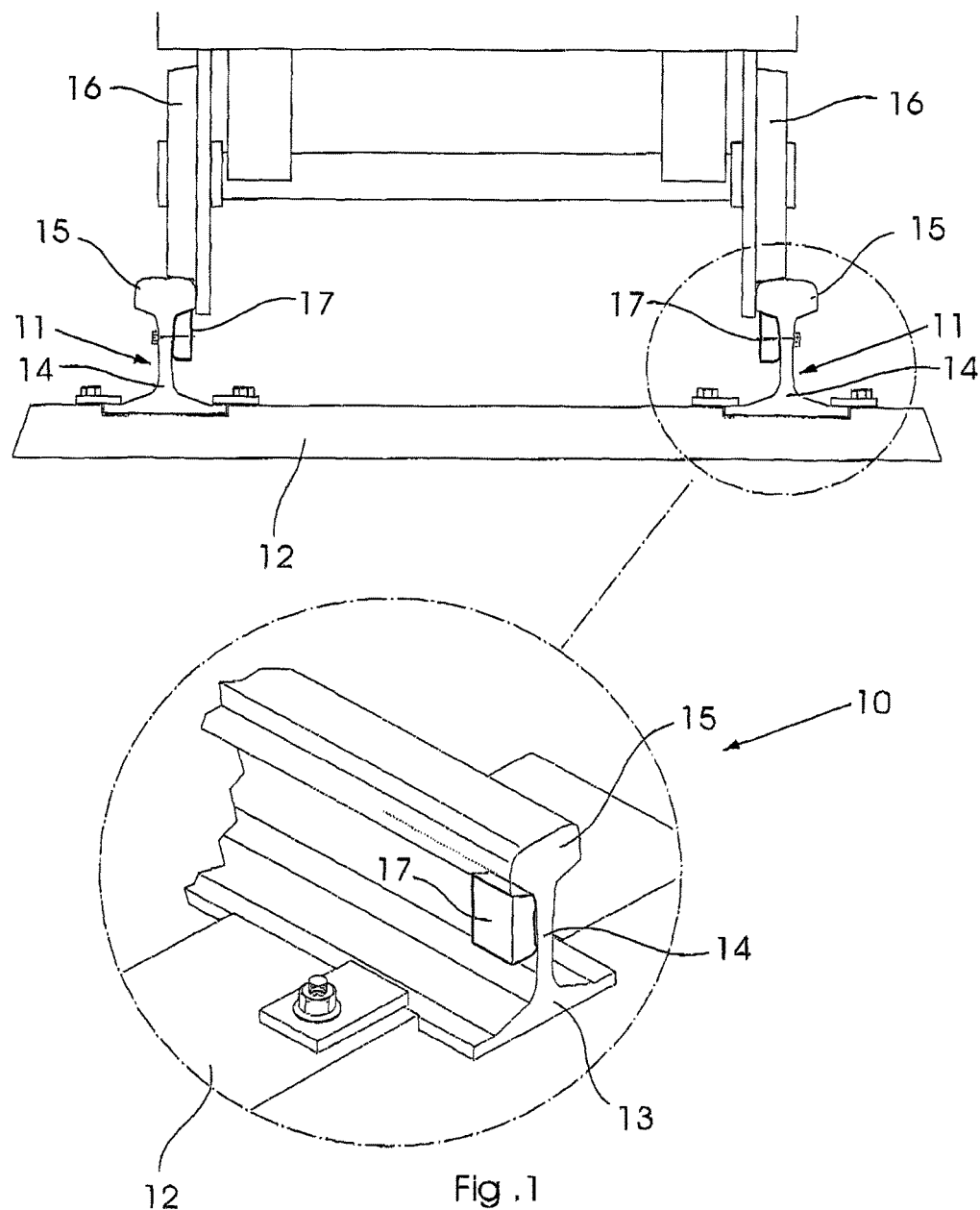
FIG. 1 shows a system in accordance with one embodiment of the present invention, the system including two piezoelectric transducers which are attached to the rails of the railway track, for monitoring and detecting cracks or breaks in the rails.

The relative small size of the transducer designed using the above design methodology enables the use of a new configuration, which is now generically described in more detail with reference to FIG. 1.

Typically, railway tracks include two parallel rails 11 that are mounted on sleepers 12. The rails 11 typically have a profile including a base 13 which rests on the sleepers 12, a web 14 extending upwardly from the base 13, and a crown 15 extending transversely from the web 14, on which the wheels 16 of a railway vehicle travel. It will however be appreciated that the system of the present invention, with modifications, can be used on any rail profile. It will be appreciated that the described embodiment relates to one particular use in a railway application, but that the system can likewise be utilised in any application involving lengths of structural steel, for example bridges and mine shafts.

In accordance with the present invention, the system 10 includes transducers 17 for detecting cracks and breaks in the rails. The transducers used in the present system are piezoelectric transducers 17. The piezoelectric transducers 17 can be permanently attached underneath the crown 15 of the rails, or attached to the web 14 of the rails 11. The piezoelectric transducers 17 are of such a geometrical size, shape and configuration that they can be attached to the rails 11 without interfering with the wheels 16 of the railway vehicle utilising the rails 11. In the preferred embodiment of the invention, these piezoelectric transducers 17 are located on the rails 11 on the inner sides of the rails 11.

The piezoelectric transducers 17 transmit ultrasonic waves which travel along the rails 11, and also operate as receivers for receiving the ultrasonic waves transmitted along the rails 11. These piezoelectric transducers 17 periodically transmit ultrasonic waves along the rails 11 to monitor the condition of the rails 11 i.e. to detect cracks and breaks in the rails 11.

The piezoelectric transducers 17 are spaced apart from one another at predetermined distances along the rails 11. Typically, the piezoelectric transducers 17 are spaced apart from one another by distances of about 1 to 3 kilometers.

The system 10 is configured such that a transducer 17 located upstream on the rail 11 transmits a signal in the form of an ultrasonic wave along the rail 11, which is received by a transducer 17 located downstream of the upstream transducer 17. If the ultrasonic wave transmitted by the upstream transducer 17 is received by the downstream transducer 17, the system 10 determines that there are no cracks or breaks in the rail 11. However, if the upstream transducer 17 transmits an ultrasonic wave which does not reach the downstream transducer 17, the system 10 determines that there is a possibility that there is a crack or break in the rail 11.

In the event that the transducer 17 located downstream does not receive the ultrasonic wave transmitted by the upstream transducer 17, the system 10 is configured to generate a signal indicating the possible presence of a crack or break in the rail 11. The signal triggers an alarm warning of the possible presence of the crack or break in the rail 11. The alarm is transmitted to a base station or the railway vehicle utilising the railway track.

In the above example the system is utilised as a signal transmission system. However, in another embodiment (not shown) the same transducers can also be used in a pulse-echo configuration where the same transducer transmits and receives a signal. The signal is transmitted by the transducer, and if there is a crack in the rail the signal will be reflected back to the same transducer, which will then also act as the receiver. The transducers developed using the design methodology described above will also be particularly suitable for this type of pulse-echo monitoring system due to the enhanced signal strength.

Irrespective of the system configuration (pulse-echo or transmission), an array of transducers (for example 4) can be provided at each predetermined location to improve the performance of the system because the additional transducers allow better control of the modes to be excited and transmission in one direction along the rail and receiving from one direction.

It will be appreciated that a combination of the transmission and pulse-echo systems would be an optimal solution. This is now possible due to the new design methodology resulting in transducers that are much better matched to the operating conditions, thus resulting in stronger signal strengths whilst also significantly reducing the size of the transducers used. In the past, larger transducers with robust designs were used to propagate the waves through the rails. This was due in part to a lack of detailed modelling of the system, and over above the physical sizes of the transducers, the design methodology used did not allow for optimal signal strength and propagation of such signal through the rails. Now, as a result of the methodology described above, the system has been optimised and one can more accurately predict the results of the wave propagation. Surprisingly, as a result of the mathematical modelling and experimentation it has been found that the transducers can be smaller than originally thought, and that the smaller transducers perform better than the older, larger and robust transducers. As a result of the smaller geometrical size, shape and configuration of the transducers, the system is optimised and has improved functionality, and in particular addresses the disadvantages mentioned above.

Figure 3:
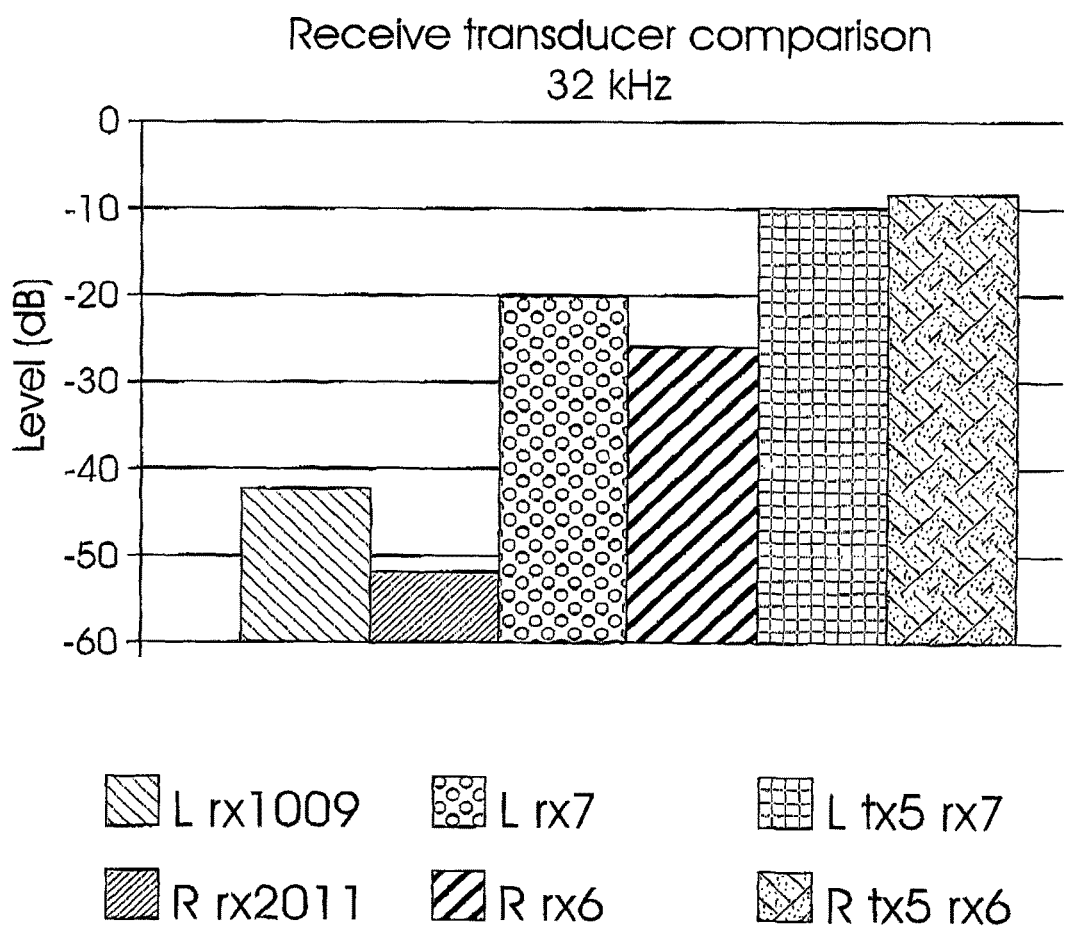
FIG. 3 shows the experimental comparison between the performance of a prior art system and the system in accordance with the invention.

A comparison between the performance of a prior art system and the new system was performed on a particular length of railway track. It was concluded that the transmit performance and receive performance of the new transducers were both 20 dB improved over the prior art transducers. The above is graphically illustrated in FIG. 3. In FIG. 3, the two bars on the left hand side of the graph represents the performance of a prior art system secured to two adjacent rails of a railway. The transmission voltage was 1300 Vp. The two bars in the middle represent the results from a combined system where the transmitters of the olds system were used, whereas the receivers were transducers designed in accordance with the new design methodology. The transmission voltage was again 1300 Vp. The two bars on the right hand side represent the results of the new system—i.e. both the transmitting and receiving transducer were designed using the new design methodology. In this case the transmission voltage was however 280 Vp. It will be noted that a 40 dB improvement was observed.

As a result of this 40 dB transmit-receive performance, it was found that the while the prior art system could only operate at 900 m spacing, on this particular rail section, the new transducers enabled operation at 2000 m spacing.

The system of the present invention addresses the problems discussed above. Firstly, the need to remove the piezoelectric transducers during routine track maintenance and the need to re-attach piezoelectric transducers after the track maintenance is eliminated. Advantageously, the piezoelectric transducers of the present invention are attached under the crown, or attached to the web of the rail on the inner sides of the rails, and thus there is no need to remove them during routine track maintenance. Moreover, the need to re-tighten the clamps after two weeks of re-attachment, according to the previous system, is eliminated. Secondly, the system performs much better than the prior art system, and can successfully be implemented for operational distances of 2000 m, on poor condition rail, where only 900 m was previously possible. This is a direct result of the new design methodology that results in larger signal transmission and improved receive sensitivity.

It will be appreciated that the above is only one embodiment of the invention and that there may be many variations without departing from the spirit and/or the scope of the invention.

The invention claimed is:

1. A computer implemented method of developing a transducer-based failure detection system, the method including the steps of:
   identifying modes of propagation and signal frequencies that can be expected to travel large distances through an elongate structural element by numerically modelling the elongate structural element to develop a numerical model of the elongate structural element;
   selecting a suitable mode of propagation and frequency of operation;
   designing a transducer that is adapted to excite the selected mode at the selected frequency;
   numerically modelling the transducer as attached to the elongate structural element by coupling the resulting numerical model of the transducer to the numerical model of the elongate structural element;
   analyzing a harmonic response of the selected mode of propagation to excitation by the transducer in order to validate the transducer design; and
   iteratively changing dimensions of transducer components in order to achieve an optimal response of the selected mode of propagation at the frequency of operation to develop a modelled transducer, and computing a predicted displacement time response of the elongate structural element to an electrical excitation of the modelled transducer.

2. The method of claim 1 in which the step of identifying modes of propagation and signal frequencies that can be expected to travel large distances through the elongate structural element comprises the use of the numerical model of the elongate structural element developed for a particular rail profile having predetermined material properties.

3. The method of claim 1 or claim 2 in which the selecting of a suitable mode of propagation and frequency of operation entails selecting as the suitable mode a mode (i) having low attenuation over a large range of frequencies, and (ii) being relatively insensitive to small changes in the rail profile.

4. The method of claim 1 or claim 2 including a verification phase that includes the further steps of:
   manufacturing a prototype in accordance with the modelled transducer;
   attaching the transducer to a predetermined length of the structural element;
   measuring a displacement response on a surface of the structural element; and
   comparing the measured response to the predicted displacement time response.

5. A system for monitoring and detecting cracks or breaks in rails of a railway track, the system including a plurality of transducers defining transmitting and receiving stations of the system, characterised in that the transducers are designed and manufactured in accordance with the method of claim 1 or claim 2.

6. A system for monitoring and detecting cracks or breaks in rails of a railway track, the system including a plurality of transducers defining transmitting and receiving stations of the system, characterised in that the transducers are designed and manufactured in accordance with the method of claim 3.

7. A system for monitoring and detecting cracks or breaks in rails of a railway track, the system including a plurality of transducers defining transmitting and receiving stations of the system, characterised in that the transducers are designed and manufactured in accordance with the method of claim 4.

8. The method of claim 1 or claim 2 further comprising manufacturing one or more transducers in accordance with the validated transducer design.

* * * * *